US010137297B2

(12) United States Patent
Gunderson

(10) Patent No.: US 10,137,297 B2
(45) Date of Patent: Nov. 27, 2018

(54) DETECTING VENTRICULAR LEAD DISLODGEMENT DURING ATRIAL FIBRILLATION

(71) Applicant: Medtronic, Inc., Minneapolis, MN (US)

(72) Inventor: Bruce D. Gunderson, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/077,435

(22) Filed: Mar. 22, 2016

(65) Prior Publication Data
US 2017/0274204 A1 Sep. 28, 2017

(51) Int. Cl.
A61N 1/08 (2006.01)
A61B 5/042 (2006.01)
A61B 5/046 (2006.01)
A61N 1/05 (2006.01)
A61N 1/39 (2006.01)

(52) U.S. Cl.
CPC ............ A61N 1/08 (2013.01); A61B 5/042 (2013.01); A61B 5/046 (2013.01); A61N 1/0563 (2013.01); A61N 1/3925 (2013.01); A61N 1/3956 (2013.01); A61N 1/3987 (2013.01); A61N 2001/083 (2013.01)

(58) Field of Classification Search
None
See application file for complete search history.

(56) References Cited

U.S. PATENT DOCUMENTS

| 5,405,363 | A | 4/1995 | Kroll et al. |
| 5,545,186 | A | 8/1996 | Olson et al. |
| 5,713,932 | A | 2/1998 | Gillberg et al. |
| 5,755,736 | A | 5/1998 | Gillberg et al. |
| 5,910,120 | A | 6/1999 | Kim et al. |
| 6,067,469 | A | 5/2000 | Kim et al. |
| 6,195,584 | B1 | 2/2001 | Hill et al. |
| 6,259,947 | B1 | 7/2001 | Olson et al. |
| 6,445,952 | B1 | 9/2002 | Manrodt et al. |
| 6,807,439 | B2 | 10/2004 | Edwards et al. |
| 6,980,860 | B2 | 12/2005 | Stadler et al. |
| 7,167,747 | B2 | 1/2007 | Gunderson et al. |
| 7,333,855 | B2 | 2/2008 | Gunderson et al. |

(Continued)

OTHER PUBLICATIONS

Iwasawa et al., "Discrimination Algorithm of an Implantable Cardioverter Defibrillator in a Case with a Lead Dislodgement", Heart Rhythm, vol. 11, 2014, PO05-208 Abstract, 2 pages.

(Continued)

Primary Examiner — Ankit D Tejani

(57) ABSTRACT

A medical device system and method for detecting dislodgement of a ventricular lead determines one or more characteristics of a cardiac signal received via the ventricular lead that are associated with dislodgement of the ventricular lead during atrial fibrillation, and detects dislodgement of the ventricular lead based on the determined characteristics. The medical device and system provides a lead dislodgment alert in response to detecting dislodgement. In some examples, an implantable medical device withholds delivery of a ventricular defibrillation therapy based on detecting dislodgement of the ventricular lead.

27 Claims, 10 Drawing Sheets

(56) References Cited

U.S. PATENT DOCUMENTS

| | | | |
|---|---|---|---|
| 7,664,550 | B2 | 2/2010 | Eick et al. |
| 8,078,277 | B2 | 12/2011 | Gunderson et al. |
| 8,660,643 | B2 | 2/2014 | Gunderson |
| 8,781,585 | B2 | 7/2014 | Gunderson et al. |
| 9,486,155 | B2 | 11/2016 | Sarkar et al. |
| 9,572,990 | B2 | 2/2017 | Gunderson |
| 2004/0220631 | A1* | 11/2004 | Burnes ............... A61N 1/3622 607/9 |
| 2011/0034983 | A1 | 2/2011 | Min et al. |
| 2012/0143278 | A1 | 6/2012 | Ryu et al. |
| 2013/0079861 | A1 | 3/2013 | Reinert et al. |
| 2014/0018873 | A1 | 1/2014 | Gunderson |
| 2014/0350422 | A1* | 11/2014 | Stewart ............. A61B 5/02405 600/513 |
| 2016/0235992 | A1 | 8/2016 | Sarkar et al. |
| 2016/0375239 | A1 | 12/2016 | Swerdlow |
| 2017/0274204 | A1 | 9/2017 | Gunderson |

OTHER PUBLICATIONS

Ruiz-Salas et al., "Inappropriate Shock Due to Late Dislocation of Electrode", International Journal of Cardiology, vol. 199, 2015, 3 pages.

Veltmann et al., "Fatal Inappropriate ICD Shock", J. Cardiovasc. Electrophysiol. vol. 18(3), 2007, 3 pages.

Cheng et al., "Acute Lead Dislodgements and In-Hospital Mortality in Patients Enrolled in the National Cardiovascula Data Registry Implantable Cardioverter Defibrillator Registry", Journal of American College of Cardiology, vol. 56, No. 20, 2010, 6 pages.

Ghani et al, "Incidence of Lead Dislodgement, Malfunction and Perforation During the First Year Following Device Implantation", Neth Heart Journal, vol. 22, 2014, 6 pages.

Zaman et al., "Early Diagnosis of Defibrillation Lead Dislodgement", JACC: Clinical Electrophysiology, 2018, 14 pages.

Kelvin Chua MBBS, et al., "Defibrillation lead dislodgement: Spectrum of clinical presentations," Heart Rhythm, 14: CPO05-48, S348, May 10-13, 2017, 3 pp. [Abstract Only].

* cited by examiner

DETECTING VENTRICULAR LEAD DISLODGEMENT DURING ATRIAL FIBRILLATION

TECHNICAL FIELD

The disclosure relates generally to medical devices and, more particularly, to a medical device, medical device system and method for detecting dislodgment of a ventricular lead during the occurrence of an atrial fibrillation episode.

BACKGROUND

Implantable medical devices (IMDs), including pacemakers and implantable cardioverter-defibrillators (ICDs), record cardiac electrogram (EGM) signals for sensing cardiac events, e.g., P-waves and R-waves. Episodes of bradycardia, tachycardia and/or fibrillation are detected from the sensed cardiac events and responded to as needed with pacing therapy or high-voltage cardioversion/defibrillation therapy. Reliable detection and treatment of potentially life-threatening ventricular tachycardia (VT) and ventricular fibrillation (VF) requires reliable sensing of cardiac signals.

Dislodgement or dislocation of a cardiac lead carrying electrodes for sensing EGM signals reduces reliable sensing and could result in erroneous sensing of cardiac signals, leading to improper detection of the cardiac rhythm and inappropriate delivery or withholding of pacing or shock therapy. While an occurrence of ventricular lead dislodgement is rare, such dislodgement could potentially cause inappropriate shock therapy to be delivered. For example, in some rare instances of a ventricular lead dislodging or being dislodged during an episode of atrial fibrillation, cardiac signals associated with the atrial fibrillation episode may be inappropriately sensed as ventricular signals, causing inappropriate detection of a ventricular fibrillation episode and the resultant delivery of therapy. In other instances, improper detection of the cardiac rhythm may cause a necessary or optimal therapy to not be delivered, such as bradycardia pacing or anti-tachycardia pacing. Accordingly, it is desirable to provide an implantable medical device and associated medical device system that is capable of detecting ventricular lead dislodgement during episodes of atrial fibrillation.

SUMMARY

Devices, systems, and techniques for identifying dislodgment of a ventricular lead during atrial fibrillation are described in this disclosure. When a ventricular lead is dislodged during atrial fibrillation, a cardiac signal sensed via the ventricular lead may demonstrate one or more characteristics associated with the dislodgement of the ventricular lead during atrial fibrillation and sensing a combination of atrial and ventricular depolarizations, such as reduced amplitude and increased variability of detected RR intervals due to sensing a combination of atrial and ventricular depolarizations. The techniques of this disclosure may include detecting dislodgement of the ventricular lead based on such characteristics.

In one example, a method of detecting dislodgement of a ventricular lead coupled to an implantable medical device comprises sensing, by sensing circuitry of the implantable medical device, a cardiac signal via the ventricular lead, determining, by processing circuitry, at least one characteristic of the cardiac signal associated with dislodgement of the ventricular lead during atrial fibrillation, detecting, by the processing circuitry, dislodgement of the ventricular lead based on the determined at least one characteristic, and providing, by the processing circuitry, a lead dislodgement alert in response to detecting the dislodgement of the ventricular lead.

In another example, a medical device system comprises a ventricular lead comprising a plurality of electrodes, and sensing circuitry configured to sense a cardiac signal via at least one of the plurality of electrodes of the ventricular lead. The system further comprises processing circuitry configured to determine at least one characteristic of the cardiac signal associated with dislodgement of the ventricular lead during atrial fibrillation, detect dislodgement of the ventricular lead based on the determined at least one characteristic, and provide a lead dislodgement alert in response to detecting the dislodgement of the ventricular lead.

In another example, a non-transitory computer-readable medium comprises instructions that, when executed by processing circuitry, cause the processing circuitry to determine at least one characteristic of the cardiac signal a cardiac signal sensed via a ventricular lead, the at least one characteristic associated with dislodgement of a ventricular lead during atrial fibrillation, detect dislodgement of the ventricular lead based on the determined at least one characteristic, and provide a lead dislodgement alert in response to detecting the dislodgement of the ventricular lead.

In another example, a medical device system comprises a ventricular lead comprising a plurality of electrodes, and an implantable medical device coupled to the ventricular lead. The implantable medical device comprises sensing circuitry configured to sense a near-field cardiac signal via at least one of the plurality of electrodes, therapy delivery circuitry configured to deliver a ventricular defibrillation therapy, and processing circuitry. The processing circuitry is configured to detect a ventricular fibrillation episode based on the sensed near-field cardiac signal, determine a variability of RR intervals of the near-field cardiac signal and an amplitude of the near-field cardiac signal in response to the ventricular fibrillation episode being detected, detect dislodgement of the ventricular lead based on the variability satisfying a variability threshold and the amplitude satisfying an amplitude threshold, and withhold delivery of a ventricular defibrillation therapy by the therapy delivery circuitry to treat the detected ventricular fibrillation episode based on the detection of dislodgement of the ventricular lead.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

DETAILED DESCRIPTION

As described above, methods, devices, and systems for identifying dislodgment of a ventricular lead during atrial fibrillation are described in this disclosure. In the following description, references are made to illustrative examples. It is understood that other examples may be utilized without departing from the scope of the disclosure.

Figure 1:
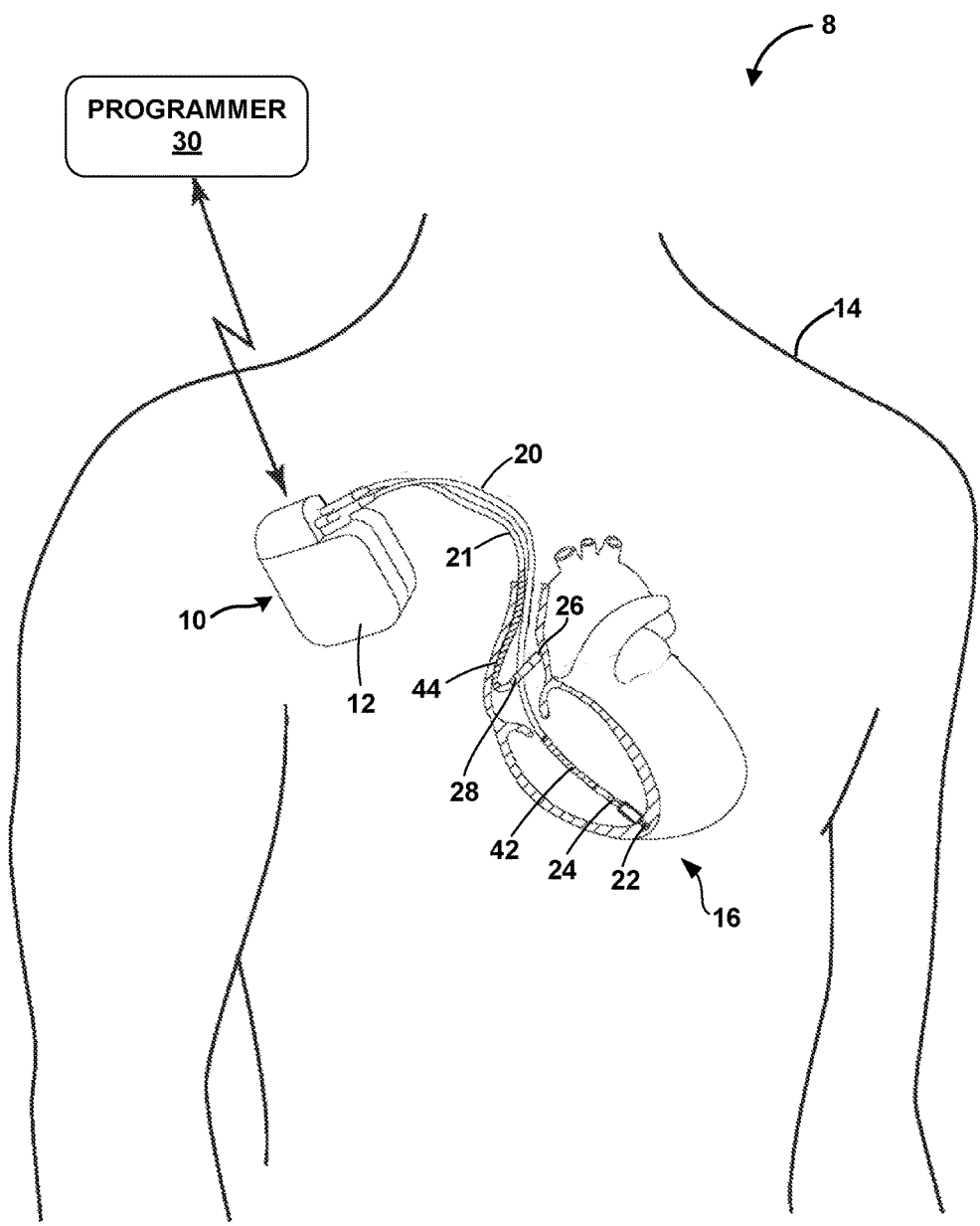
FIG. 1 is an example schematic diagram of an implantable medical device system configured to detect dislodgement of a ventricular lead during atrial fibrillation.

FIG. 1 is an example schematic diagram of an implantable medical device system configured to detect dislodgement of a ventricular lead during atrial fibrillation. As illustrated in FIG. 1, a medical device system 8 for sensing cardiac events (e.g. P-waves and R-waves) and detecting tachyarrhythmia episodes, as well as detecting dislodgement of a ventricular lead during atrial fibrillation, may include an implantable medical device (IMD) 10, a ventricular lead 20 and an atrial lead 21. In one example, IMD 10 may be an implantable cardioverter-defibrillator (ICD) capable of delivering pacing, cardioversion and defibrillation therapy to the heart 16 of a patient 14.

Ventricular lead 20 and atrial lead 21 are electrically coupled to IMD 10 and extend into the patient's heart 16. Ventricular lead 20 includes electrodes 22 and 24 shown positioned on the lead in the patient's right ventricle (RV) for sensing ventricular EGM signals and pacing in the RV. Atrial lead 21 includes electrodes 26 and 28 positioned on the lead in the patient's right atrium (RA) for sensing atrial EGM signals and pacing in the RA. Such a medical device and medical device system is described, for example, in commonly assigned U.S. Patent Publication No. 2014/0018873, which is incorporated herein by reference in its entirety.

Ventricular lead 20 additionally carries a high voltage coil electrode 42, and atrial lead 21 carries a high voltage coil electrode 44, used to deliver cardioversion and defibrillation shock pulses. In other examples, ventricular lead 20 may carry both of high voltage coil electrodes 42 and 44, or may carry a high voltage coil electrode in addition to those illustrated in the example of FIG. 1. Both the ventricular lead 20 and the atrial lead 21 may be used to acquire cardiac EGM signals from the patient 14 and to deliver therapy in response to the acquired data. Medical device system 8 is shown as a dual chamber ICD, but in some embodiments, system 8 may be a multi-chamber system including a coronary sinus lead extending into the right atrium, through the coronary sinus and into a cardiac vein to position electrodes along the left ventricle (LV) for sensing LV EGM signals and delivering pacing pulses to the LV. In other examples, system 8 may be a single chamber system, or otherwise not include atrial lead 21.

In some examples, ventricular lead 20 is anchored along the right ventricular apex or the intraventricular septum by a fixation member (not shown), such as tines positioned at the distal end of lead 20 in the vicinity of electrode 22 or a helical screw, which may also serve as electrode 22. Use of a fixation member generally anchors the position of ventricular lead 20 in the RV. However, on rare occasions, ventricular lead 20 may become dislodged from the ventricular myocardium and shift or migrate within the ventricle or toward or within the right atrium. When this occurs, the EGM signal received by IMD 10 from electrodes 22 and 24 will change due to the altered location of electrodes 22 and 24, which may result in electrical activity of the atria of heart being inadvertently sensed via ventricular lead 20 as ventricular activity. Such a situation of sensing both atrial and ventricular depolarizations as ventricular signals can be especially problematic during the occurrence of atrial fibrillation, since the result could be inappropriate detection of a ventricular fibrillation episode and unnecessary delivery of ventricular defibrillation therapy. Techniques for detecting cardiac lead dislodgement, particularly dislodgement of a ventricular lead during the occurrence of atrial fibrillation, will be described herein.

Implantable medical device circuitry configured for performing the methods described herein and an associated battery or batteries are housed within a sealed housing 12. Housing 12 may be conductive so as to serve as an electrode for use as an indifferent electrode during pacing or sensing or as an active electrode during defibrillation. As such, housing 12 is also referred to herein as "housing electrode" 12.

EGM signal data, cardiac rhythm episode data, and lead dislodgement data acquired by IMD 10 can be transmitted to an external device 30. External device 30 may be a computing device, e.g. used in a home, ambulatory, clinic, or hospital setting, to communicate with IMD 10 via wireless telemetry. External device 30 may be coupled to a remote patient monitoring system, such as Carelink®, available from Medtronic plc, of Dublin, Ireland. External device 30 may be, as examples, a programmer, external monitor, or consumer device, e.g., smart phone.

External device 30 may be used to program commands or operating parameters into IMD 10 for controlling IMD function, e.g., when configured as a programmer for IMD 10. External device 30 may be used to interrogate IMD 10 to retrieve data, including device operational data as well as physiological data accumulated in IMD memory. The interrogation may be automatic, e.g., according to a schedule, or in response to a remote or local user command. Programmers, external monitors, and consumer devices are examples of external devices 10 that may be used to interrogate IMD 10. Examples of communication techniques used by IMD 10 and external device 30 include radiofrequency (RF) telemetry, which may be an RF link established via Bluetooth, WiFi, or medical implant communication service (MICS).

One or more components of system 8 may identify dislodgment of ventricular lead 20 during atrial fibrillation using the techniques described in this disclosure. For example, IMD 10 may sense a ventricular EGM via ventricular lead 20, e.g., a near-field EGM sensed via tip electrode 22 and ring electrode 24 of ventricular lead 20, and one or more of IMD 10 and external device 30 may determine whether ventricular lead 20 is dislodged based on the ventricular EGM. External device 30 may receive the ventricular EGM and/or data representative of the ventricular EGM from IMD 10 via RF telemetry.

For example, IMD 10 or external device 30 may identify one or more characteristics of the ventricular EGM that are associated with the dislodgement of ventricular lead 20 during atrial fibrillation, such as reduced signal amplitude and/or increased variability of detected RR intervals, which may be due to sensing both atrial and ventricular depolarizations in the near-field EGM sensed via ventricular lead 20. IMD 10 or external device 30 may detect dislodgement of ventricular lead 20 based on such characteristics meeting one or more respective thresholds. IMD 10 and/or external device 30 may provide a lead dislodgement alert in response to detecting dislodgement of ventricular lead 20. In some examples, IMD 10 may alter its sensing or therapy delivery, such as withholding a ventricular defibrillation therapy, in response to detecting dislodgement of ventricular lead 20.

Figure 2:
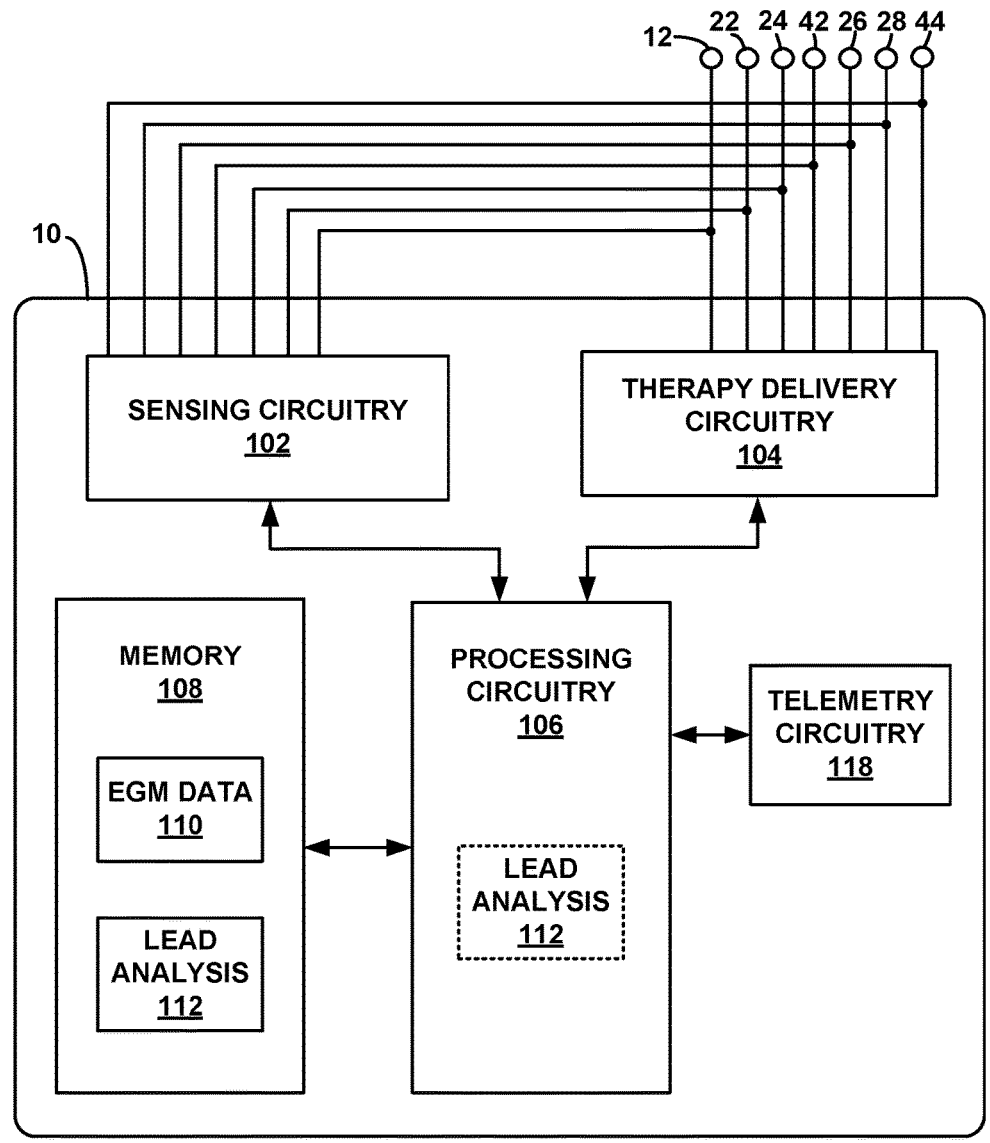
FIG. 2 is a functional block diagram of an example implantable medical device configured to detect dislodgement of a ventricular lead during atrial fibrillation.

FIG. 2 is a functional block diagram of an example configuration of IMD 10 that detects dislodgement of a ventricular lead (e.g., ventricular lead 20 of FIG. 1) during atrial fibrillation. In the example illustrated by FIG. 2, IMD 10 includes sensing circuitry 102, therapy delivery circuitry 104, processing circuitry 106 and associated memory 108, and telemetry circuitry 118.

Processing circuitry 106 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 106 may include multiple components, such as any combination of one or more microprocessors, one or more DSPs, one or more ASICs, or one or more FPGAs, as well as other discrete or integrated logic circuitry, and/or analog circuitry.

Memory 108 may store program instructions, which may include one or more program modules, which are executable by processing circuitry 106. When executed by processing circuitry 106, such program instructions may cause processing circuitry 106 and IMD 10 to provide the functionality ascribed to them herein. The program instructions may be embodied in software, firmware and/or RAMware. Memory 108 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Sensing circuitry 102 is configured to receive cardiac electrical signals from selected combinations of two or more of electrodes 22, 24, 26, 28, 42 and 44 carried by the ventricular lead 20 and atrial lead 21, along with housing electrode 12. Sensing circuitry 102 is configured to sense cardiac events attendant to the depolarization of myocardial tissue, e.g. P-waves and R-waves. Sensing circuitry 102 may include a switching circuitry for selectively coupling electrodes 12, 22, 24, 26, 28, 42, 44 to sensing circuitry 102 in order to monitor electrical activity of heart 16. The switching circuitry may include a switch array, switch matrix, multiplexer, or any other type of switching device suitable to selectively couple one or more of the electrodes to sensing circuitry 102. In some examples, processing circuitry 106 selects the electrodes to function as sense electrodes, or the sensing vector, via the switching circuitry within sensing circuitry 102.

Sensing circuitry 102 may include multiple sensing channels, each of which may be selectively coupled to respective combinations of electrodes 12, 22, 24, 26, 28, 42, 44 to detect electrical activity of a particular chamber of heart 16, e.g., an atrial sensing channel and a ventricular sensing channel. Each sensing channel may be configured to amplify, filter and rectify the cardiac electrical signal received from selected electrodes coupled to the respective sensing channel to detect cardiac events, e.g., P-waves and/or R-waves. For example, each sensing channel may include one or more filters and amplifiers for filtering and amplifying a signal received from a selected pair of electrodes. The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter.

Sensing circuitry 102 outputs an indication to processing circuitry 106 in response to sensing of a cardiac event, in the respective chamber of heart 16 (e.g., detected P-waves or R-waves). In this manner, processing circuitry 106 may receive detected cardiac event signals corresponding to the occurrence of detected R-waves and P-waves in the respective chambers of heart 16. Indications of detected R-waves and P-waves may be used for detecting ventricular and/or atrial tachyarrhythmia episodes, e.g., ventricular or atrial fibrillation episodes. Sensing circuitry 102 may also pass one or more digitized EGM signals to processing circuitry 106 for analysis, e.g., for use in cardiac rhythm discrimination. Processing circuitry 106 may use the indications of R-waves and/or the digitized ventricular EGM signals to detect dislodgement of ventricular lead 20 during atrial fibrillation. Indications of R-wave and P-wave timing, as well as digitized EGMs, may be stored in memory 108 as EGM data 110.

Memory 108 may also store a lead analysis module 112. Lead analysis module 112 may be a software, firmware, or RAMware module executable by processing circuitry 106 to cause processing circuitry 106 to provide functionality related to identifying dislodgement of ventricular lead 20 during atrial fibrillation as described herein. Such functionality may include identifying characteristics of a ventricular EGM signal, detecting dislodgment based on the characteristics, providing an alert, and/or modifying sensing or therapy provided by IMD 10, as described herein. Processing circuitry 106 may load lead analysis module 112 from memory 108 (shown by the dotted lead analysis module 112 within processing circuitry 106) and execute the loaded lead analysis module 112 in response to an event, such as detection of atrial fibrillation via an atrial EGM, detection of ventricular fibrillation via a ventricular EGM, or a command from external device 30 received via telemetry circuitry 118. In other examples, processing circuitry 106 may execute lead analysis module 112 periodically, e.g., according to a schedule, or substantially continuously, throughout the operation of IMD 10.

Processing circuitry 106 may control therapy delivery circuitry 104 to deliver electrical therapy, e.g., cardiac pacing, anti-tachyarrhythmia therapy, or shock pulses, to heart 16 according to therapy parameters stored in memory 108. Therapy delivery circuitry 104 is electrically coupled to electrodes 12, 22, 24, 26, 28, 42, 44, and is configured to generate and deliver electrical therapy to heart 16 via selected combinations of electrodes 12, 22, 24, 26, 28, 42, 44. Therapy delivery circuit 104 may include charging circuitry, one or more charge storage devices, such as one or more high voltage capacitors and/or one or more low voltage capacitors, and switching circuitry that controls when the capacitor(s) are discharged to selected combinations of electrodes 12, 22, 24, 26, 28, 42, 44. Charging of capacitors to a programmed pulse amplitude and discharging of the capacitors for a programmed pulse width may be performed by therapy delivery circuit 104 according to control signals received from processing circuitry 106.

Memory 108 stores intervals, counters, or other data used by processing circuitry 106 to control the delivery of pacing pulses by therapy delivery circuitry 104. Such data may include intervals and counters used by processing circuitry 106 to control the delivery of pacing pulses to heart 16. The intervals and/or counters are, in some examples, used by processing circuitry 106 to control the timing of delivery of pacing pulses relative to an intrinsic or paced event in another chamber. Memory 108 also stores intervals for controlling cardiac sensing functions such as blanking intervals and refractory sensing intervals and counters for counting sensed events for detecting cardiac rhythm episodes. Events sensed by sense amplifiers included in sensing circuitry 102 are identified in part based on their occurrence outside a blanking interval and inside or outside of a refractory sensing interval. Events that occur within predetermined interval ranges are counted for detecting cardiac rhythms. According to embodiments described herein, sensing circuitry 102, therapy circuitry 104, memory 108, and processing circuitry 106 are configured to use timers and counters for measuring sensed event intervals and determining event patterns for use in detecting possible ventricular lead dislodgement.

Processing circuitry 106 may receive analog and/or digitized EGM signals and sensed event signals corresponding to detected R-waves and P-waves from sensing circuitry 102 for use in identifying possible dislodgement or dislocation of ventricular lead 20, e.g., when executing lead analysis module 112. As will be described herein, processing circuitry 106 may detect dislodgement of ventricular lead 20 during atrial fibrillation based on an amplitude of the ventricular EGM signal, e.g., an amplitude of R-waves in the digitized ventricular EGM, and/or variability of RR intervals indicated by the sensing of R-waves by sensing circuitry 102.

Processing circuitry 106 may respond to a lead dislodgement by generating a patient or clinician alert, which may be transmitted by telemetry circuitry 118, by withholding delivery of therapy, or both, as will be described below. Processing circuitry 106 may additionally respond to a possible lead dislodgement by adjusting cardiac rhythm episode detection criteria and/or adjusting the control of therapy delivery module 104 to avoid inappropriate delivery or withholding of a therapy.

Telemetry circuitry 118 is used to communicate with external device 30, for transmitting data accumulated by IMD 10 and for receiving interrogation and programming commands from external device 30. Under the control of processing circuitry 106, telemetry circuitry 118 may transmit an alert to notify a clinician and/or the patient that IMD 10 has detected a possible ventricular lead dislodgement. This alert enables the clinician to perform additional testing to confirm the dislodgement and to intervene if necessary to reposition or replace the lead, or to prevent unnecessary defibrillation therapy from being delivered to the patient. In other embodiments, IMD 10 may be equipped with alert circuitry configured to emit a sensory alert perceptible by the patient, e.g. a vibration or an audible tone, under the control of processing circuitry 106 to alert the patient to the possibility of a ventricular lead displacement.

As described above, in instances of a ventricular lead dislodging or being dislodged during an episode of atrial fibrillation, the ventricular lead may migrate from the ventricle towards the atrium, increasing the likelihood that cardiac signals associated with the atrial fibrillation episode (e.g., atrial cardiac events) may be inappropriately sensed as ventricular events, causing inappropriate sensing of a ventricular tachyarrhythmia episode, such as ventricular fibrillation, and resulting in an inappropriate delivery of ventricular fibrillation therapy. Accordingly, in some examples, processing circuitry 106 controls therapy delivery circuitry 104 to withhold the delivery of a therapy for treating ventricular arrhythmias, e.g., a ventricular defibrillation shock for treating a detected ventricular fibrillation episode, based on detecting dislodgement of ventricular lead 20. In some examples, processing circuitry 106 determines characteristics of the ventricular EGM associated with lead dislodgement in response to detection of a ventricular fibrillation episode and, if dislodgement of ventricular lead 20 is detected, controls therapy delivery circuitry 104 to withhold delivery of a defibrillation shock to treat the detected ventricular fibrillation based on the detection of lead dislodgement.

In some examples, processing circuitry 106 initiates the analysis to identify characteristics of the ventricular EGM indicative of dislodgment of ventricular lead at the time of implant of ventricular lead 20 in the patient 14, either in response to a command from external device 30, or automatically. Since the likelihood of lead dislodgement occurring is greatest within the first few months after implant, processing circuitry 106 may initiate the lead dislodgement surveillance techniques described herein at the time of implant of ventricular lead 20 in the patient 14, and then turn of the lead dislodgment surveillance after a predetermined time period subsequent to implant, e.g., after three, four, or six months, as examples, either in response to commands from external device 30 and/or automatically.

In some examples, to further increase the likelihood that dislodgment of ventricular lead may be detected during the occurrence of atrial fibrillation, processing circuitry 106 initiates the lead dislodgement surveillance techniques described herein based on an atrial fibrillation episode having previously been detected in patient 14, e.g., by processing circuitry 106 based on an atrial EGM, or by some other device or clinician and indicated to processing circuitry 106 via telemetry circuitry 118. In some examples in which processing circuitry 106 initiates the lead dislodgement surveillance techniques based on an atrial fibrillation episode having previously been detected in patient 14, processing circuitry 106 may still end the lead dislodgment surveillance after the predetermined period of time, e.g., after three, four, or six months, from implant of ventricular lead 20. In such examples, processing circuitry 106 may initiate the lead dislodgement surveillance techniques based on both an atrial fibrillation episode having previously been detected in patient 14 and the ventricular lead having been implanted for less than the predetermined time period.

In some examples, processing circuitry 106 may enable or disable a withholding feature, e.g., based on whether ventricular lead 20 has been implanted for less than the predetermined time period and/or whether an atrial fibrillation episode has previously been detected in patient 14 in the manner described above. In some examples, processing circuitry 106 performs the lead dislodgement surveillance techniques described herein when the withholding feature is enabled, and does not perform the lead dislodgement surveillance techniques described herein when the withholding feature is disabled. In other examples, processing circuitry 106 may perform lead surveillance and provide alerts in response to detecting lead dislodgment whether or not the withholding feature is enabled, but will only withhold therapy, e.g., a defibrillation shock, in response to detecting lead dislodgement, if the withholding feature is enabled.

Figure 3:
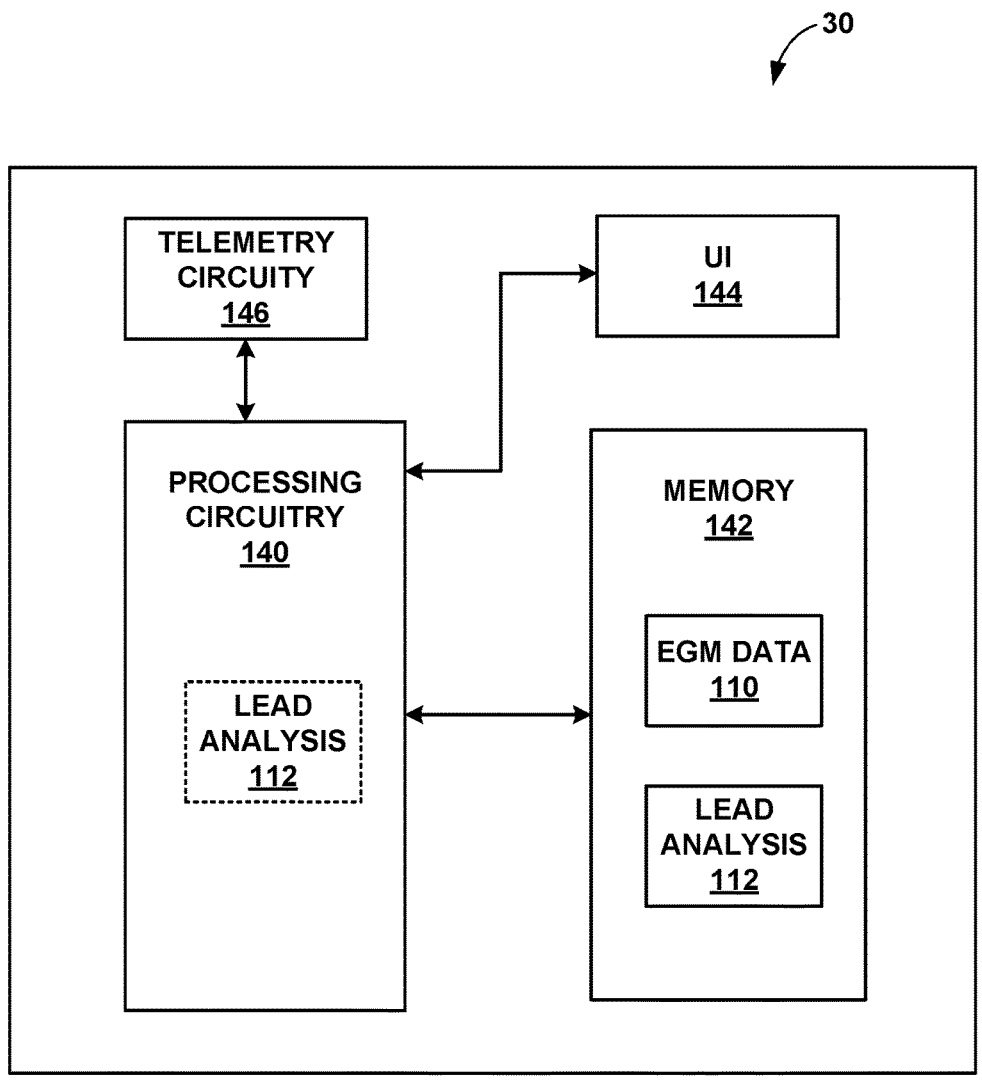
FIG. 3 is a functional block diagram of an example programming device configured to communicate with an implantable medical device.

FIG. 3 is a functional block diagram of an example configuration of external device 30. In the example of FIG. 3, external device 30 includes processing circuitry 140, memory 142, user interface (UI) 144, and telemetry circuitry 146. External device 30 may be a dedicated hardware device with dedicated software for the programming and/or interrogation of IMD 10. Alternatively, external device 30 may be an off-the-shelf computing device, e.g., running an application that enables external device 30 to program and/or interrogate IMD 10.

In some examples, a user uses external device 30 to select or program values for operational parameters of IMD 10, e.g., for cardiac sensing, therapy delivery, and lead dislodgment detection. In some examples, a user uses external device 30 to receive data collected by IMD 10, such as cardiac EGM data 110 or other operational and performance data of IMD 10. The user may also receive lead dislodgment alerts provided by IMD 10, or data regarding modifications to sensing or therapy made by IMD 10 in response to detecting lead dislodgement, e.g., indications of when IMD 10 withheld defibrillation therapy, via external device 30. The user may interact with external device 30 via UI 144, which may include a display to present a graphical user interface to a user, and a keypad or another mechanism for receiving input from a user. External device 30 may communicate wirelessly with IMD 10 using telemetry circuitry 146, which may be configured for RF communication with telemetry circuitry 118 of IMD 10.

Processing circuitry 140 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 106 may include multiple components, such as any combination of one or more microprocessors, one or more DSPs, one or more ASICs, or one or more FPGAs, as well as other discrete or integrated logic circuitry, and/or analog circuitry.

Memory 142 may store program instructions, which may include one or more program modules, which are executable by processing circuitry 140. When executed by processing circuitry 140, such program instructions may cause processing circuitry 140 and external device 30 to provide the functionality ascribed to them herein. The program instructions may be embodied in software, firmware and/or RAMware. Memory 142 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In some examples, processing circuitry 140 of external device 30 may be configured to provide some or all of the functionality ascribed to processing circuitry 106 of IMD 10 herein. For example, processing circuitry 140 may receive EGM data 110 of a ventricular EGM signal sensed via ventricular lead 20 from IMD 10 via telemetry circuitry 144, and may store the EGM data 110 in memory 142. EGM data 110 may be current EGM data, or data previously collected and stored by IMD 10. Using EGM data 110, processing circuitry 140 of external device 30 may identify characteristics of the ventricular EGM indicative of dislodgment of a ventricular lead during atrial fibrillation, and detect dislodgment of ventricular lead 20 based on such characteristics. Based on the detection of dislodgment, processing circuitry 140 may provide an alert to a user, e.g., via UI 144. In some examples, the lead dislodgment detection functionality may be provided by lead analysis module 112, which may a software module stored in memory 142, and loaded and executed by processing circuitry 140 (as illustrated by the dotted outline lead analysis module 112 within processing circuitry 140), e.g., in response to a command from the user.

Figure 4:
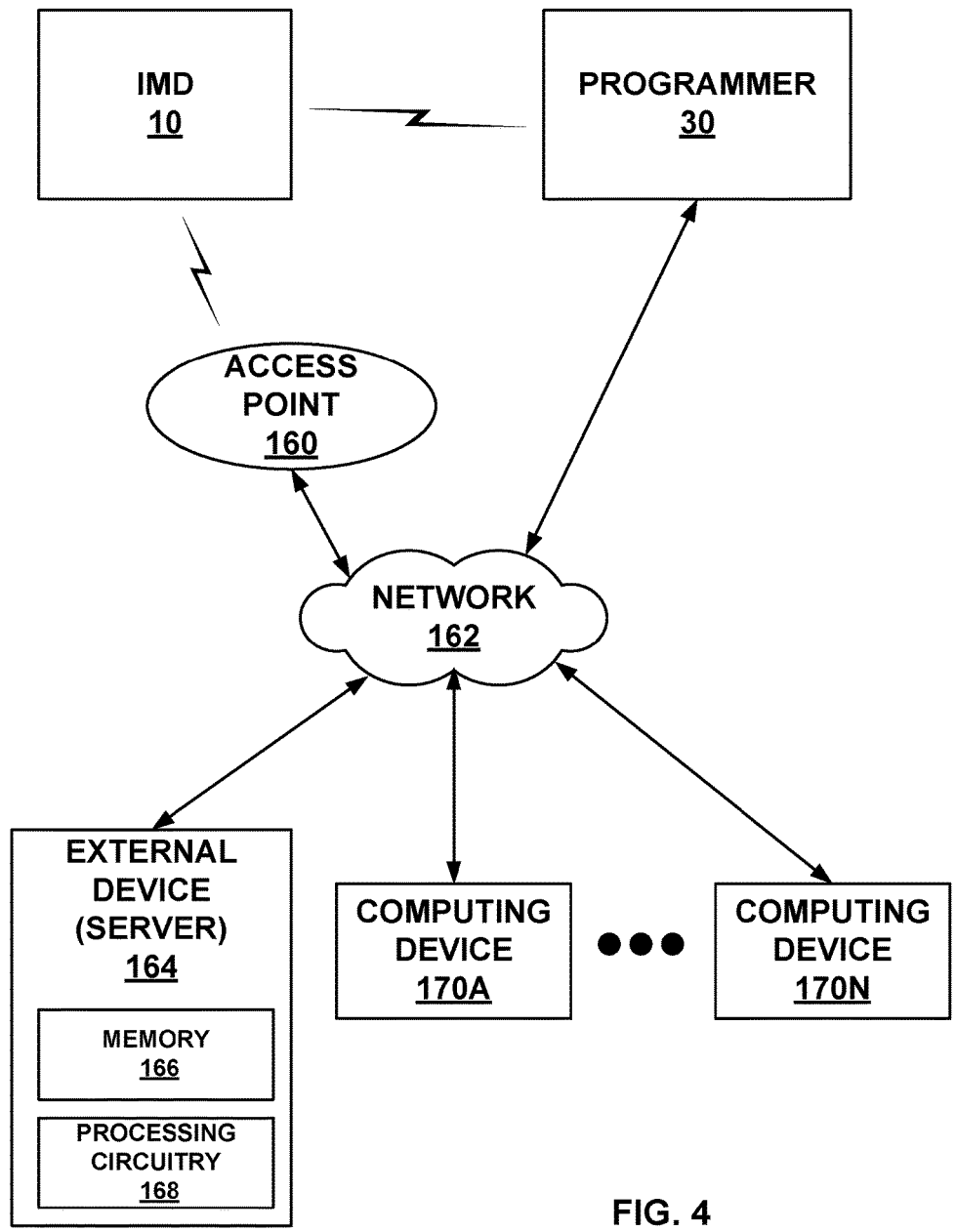
FIG. 4 is a functional block diagram illustrating an example system that includes external computing devices, such as a server and one or more other computing devices, that are coupled to the IMD and programmer shown in FIG. 1 via a network

FIG. 4 is a functional block diagram illustrating an example system that includes external computing devices, such as a server 164 and one or more other computing devices 170A-170N, that are coupled to IMD 10 and external device 30 via a network 162. In this example, IMD 10 may use its telemetry module 118 to, e.g., at different times and/or in different locations or settings, communicate with external device 30 via a first wireless connection, and to communication with an access point 160 via a second wireless connection. In the example of FIG. 4, access point 160, external device 30, server 164, and computing devices 170A-170N are interconnected, and able to communicate with each other, through network 162.

Access point 160 may comprise a device that connects to network 162 via any of a variety of connections, such as telephone dial-up, digital subscriber line (DSL), or cable modem connections. In other examples, access point 160 may be coupled to network 162 through different forms of connections, including wired or wireless connections. In some examples, access point 160 may be co-located with patient 14. Access point 160 may interrogate IMD 10, e.g., periodically or in response to a command from patient 14 or network 162, to retrieve EGM data 110 or other operational data from IMD 10. Access point 160 may provide the retrieved data to server 164 via network 162.

In some cases, server 164 may be configured to provide a secure storage site for data that has been collected from IMD 10 and/or external device 30, such as the Internet. In some cases, server 164 may assemble data in web pages or other documents for viewing by trained professionals, such as clinicians, via computing devices 170A-170N. The illustrated system of FIG. 4 may be implemented, in some aspects, with general network technology and functionality similar to that provided by the Medtronic CareLink® Network developed by Medtronic plc, of Dublin, Ireland.

In some examples, one or more of access point 160, server 164, or computing devices 170 may be configured to perform, e.g., may include processing circuitry configured to perform, some or all of the techniques described herein relating to detecting dislodgment of a ventricular lead. In the example of FIG. 4, server 164 includes a memory 166 to store EGM data received from IMD 10, and processing circuitry 168, which may be configured to provide some or all of the functionality ascribed to processing circuitry 106 of IMD 16 herein. For example, processing circuitry 168 may identify characteristics of the ventricular EGM indicating dislodgment of a ventricular lead during atrial fibrillation based on the EGM data received from IMD 10. Processing circuitry 168 may identify dislodgment of ventricular lead 20 based on the identified characteristics, and may provide a lead dislodgment alert to a user, e.g., via external device 30 or one of computing devices 170.

Figure 5:
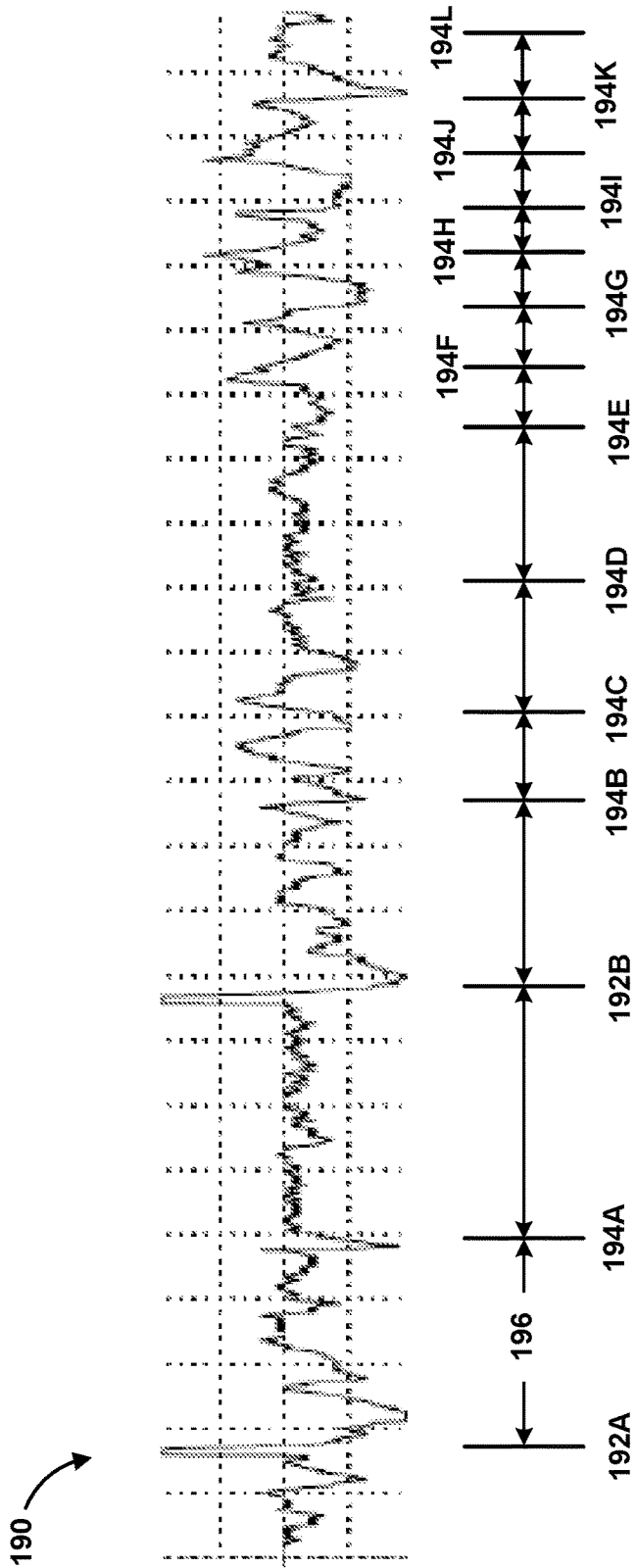
FIG. 5 is a timing diagram illustrating an example cardiac signal sensed via a ventricular lead before and after dislodgement of the ventricular lead during atrial fibrillation.

FIG. 5 is a timing diagram illustrating an example cardiac signal 190, e.g., ventricular EGM, sensed via a ventricular lead, e.g., ventricular lead 20, when dislodged and during an atrial fibrillation episode. FIG. 5 also illustrates instances at which therapy delivery circuitry 104 of IMD 10 delivered pacing pulses 192A and 192B (collectively "pacing pulses 192") via ventricular lead 20, and instances at which sensing circuitry 102 of IMD 10 detected R-waves 194A-194L (collectively "R-waves 194") in cardiac signal 190. FIG. 5 also illustrates RR intervals 196, only one of which is labeled in FIG. 5 for ease of illustration, determined by processing circuitry described herein, such as processing circuitry 106 of IMD 10. An RR interval is the interval between consecutive ventricular events whether those events are a result of pacing or of intrinsic conduction. In other words, an RR interval may be an interval between consecutive R-waves 194, between consecutive pacing pulses 192, or between a consecutive R-wave 194 and pacing pulse 192, in either order.

Although an atrial EGM is not illustrated in FIG. 5, an atrial fibrillation episode of heart 16 was ongoing during the acquisition of the illustrated ventricular cardiac signal 190. Furthermore, the ventricular lead, e.g., ventricular lead 20, used to acquire ventricular cardiac signal 190 was dislodged during acquisition of cardiac signal 190. Consequently, as illustrated in FIG. 5, cardiac signal 190 demonstrates characteristics associated with dislodgement of ventricular lead 20 during atrial fibrillation.

For example, cardiac signal 190 may be a near-field EGM, and the amplitudes of the features of cardiac signal 190 detected by sensing circuitry 102 as R-waves 194 may be relatively lower and more variable when ventricular lead 20 is dislodged then R-waves detected by sensing circuitry 102 prior to the dislodgment of ventricular lead 20. The features of cardiac signal 190 detected by sensing circuitry 102 as R-waves 194 when ventricular lead 20 is dislodged during atrial fibrillation may include actual ventricular depolarizations, and atrial fibrillation signals incorrectly detected as R-waves. The amplitudes of these features may be relatively low due to the electrodes of ventricular lead 20, e.g., tip electrode 22, being in contact with neither of the ventricular or atrial myocardium, and may be variable due to variable proximity of dislodged ventricular lead 20 to ventricular or atrial myocardium during the cardiac cycle. Additionally, the atrial fibrillation signals may generally have lower amplitudes than atrial depolarizations during sinus rhythm.

Processing circuitry 106 (or any other processing circuitry described herein that receives a digitized version of cardiac signal 190 from IMD 10) may determine amplitudes of R-waves 194 detected by sensing circuitry 102 via ventricular lead 20 as a characteristic associated with dislodgement of ventricular lead 20 during atrial fibrillation. For example, the processing circuitry may determine the R-wave amplitude to be an absolute value of cardiac signal 190, e.g., near-field ventricular EGM, relative to a baseline at the point of detection of an R-wave 194 or a peak, mean or other amplitude value within a window of cardiac signal 190 around the point of detection of the R-wave.

Processing circuitry 106 may detect dislodgement of ventricular lead 20 based on determined amplitudes of R-waves 194, e.g., detected by sensing circuitry 102 in near-field ventricular EGM via ventricular lead 20, such as based on whether the amplitudes of R-waves 194 are less than an amplitude threshold. The amplitude threshold may be a fixed, predetermined value, or may be a variable value, e.g., determined based on amplitudes of R-waves 194, or cardiac signal 190 generally, when ventricular lead 20 was not dislodged. In some examples, processing circuitry, e.g., processing circuitry 106, determines the amplitude threshold based on the amplitudes of R-waves detected during one or more prior induced or spontaneous ventricular fibrillation episodes of patient 14. For example, the amplitude threshold may be a percentage, e.g., 50%, of the amplitudes of R-waves detected during one or more prior induced or spontaneous ventricular fibrillation episodes of patient 14. In one example, the amplitude threshold is 1 mV.

In some examples, processing circuitry 106 detects dislodgement of ventricular lead 20 based on the amplitudes of a threshold percentage or fraction of a group of R-waves 194 that are part of an episode, e.g., a group of R-waves 194 leading up to detection of ventricular fibrillation, being less than the threshold amplitude. In some examples, the group of R-waves 194 includes the R-waves 194 in a detected ventricular fibrillation episode that were associated with R-R intervals less than the ventricular fibrillation interval threshold. In one example, the number of R-waves 194 whose amplitude is considered is 18, e.g., the R-waves 194 associated with the 18 RR intervals of 24 consecutive RR intervals below the ventricular fibrillation interval threshold that led to detection of a ventricular fibrillation episode. In one example, processing circuitry 106 detects dislodgement of ventricular lead 20 based on at least 25% of the amplitudes of the group of R-waves 194 being less than the amplitude threshold.

As another example, the variability of RR intervals 196 detected via ventricular lead 20 when the ventricular lead is dislodged may be greater than the variability of RR intervals 196 before dislodgement of ventricular lead 20, e.g., greater than the variability of RR intervals 196 detected via ventricular lead 20 during ventricular fibrillation episodes before dislodgment of ventricular lead 20. Processing circuitry 106 (or any other processing circuitry described herein that receives indications of the timing of pacing pulses 192 and R-waves 194 from IMD 10) may determine one or more parameters indicative of the variability of RR intervals 196 as a characteristic associated with dislodgement of ventricular lead 20 during atrial fibrillation. For example, processing circuitry 106 may determine at least one of a modesum of the RR intervals 196 or a ratio of a maximum and a minimum of the RR intervals 196 within a group of RR intervals 196 as parameters indicative of the variability of RR intervals 196. The group of RR intervals may be consecutive RR intervals 196, which may have preceded detection of ventricular fibrillation, as described above.

To determine the modesum, in one example, processing circuitry 106 groups interval values into bins, each bin associated with a range of interval values, and determines the percentage of the values of RR intervals 196 that are within the two most populated interval value bins. In one example, processing circuitry 106 detects dislodgment of ventricular lead 20 based on the modesum of RR intervals 196 being less than the modesum threshold, e.g., 50%. In some examples, the ratio between the maximum and minimum of the RR intervals 196 is a ratio of the maximum to the minimum, and processing circuitry 106 detects dislodgment of ventricular lead 20 based on the ratio exceeding a ratio threshold, e.g., 2.0. In other examples, the ratio between the maximum and minimum of the RR intervals 196 is a ratio of the minimum to the maximum, and processing circuitry 106 detects dislodgment of ventricular lead 20 based on the ratio being less than a ratio threshold.

In some examples, processing circuitry 106 may determine differences between consecutive RR intervals 196 of the group of RR intervals 196, and may determine a number or percentage of the determined differences that exceed a threshold difference as a parameter indicative of the variability of RR intervals 196. In such examples, processing circuitry 106 detects dislodgment of ventricular lead 20 based on the number or percentage of supra-threshold differences exceeding a threshold number or percentage. In general, processing circuitry 106 may detect dislodgement of ventricular lead 20 based on the variability of RR intervals 196 satisfying a variability threshold.

In some examples, in response to a group of RR intervals 196 satisfying a programmable number of intervals to detect (NID) criterion for detecting ventricular fibrillation (e.g., 18 RR intervals 196 out of 24 consecutive RR intervals 196 being shorter than the ventricular fibrillation threshold), processing circuitry 106 determines the amplitude of R-waves 194 and variability of RR-intervals 196 leading to the satisfaction of the NID criterion, such as consecutive R-waves or RR intervals prior to detection, or the specific RR intervals 196 (e.g., the 18 RR intervals 196) that were shorter than the ventricular fibrillation threshold and R-wave amplitudes associated with those RR intervals.

Figure 6:
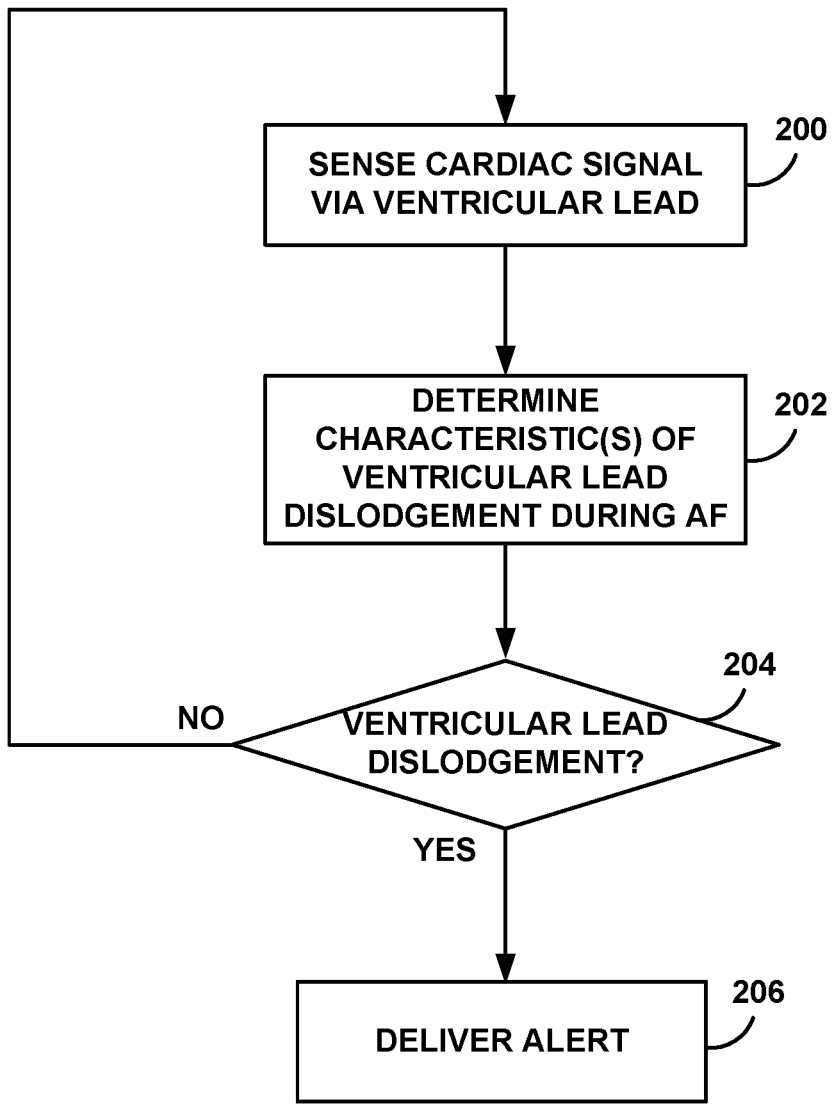
FIG. 6 is a flowchart of an example technique for identifying dislodgment of a ventricular lead during atrial fibrillation.

FIG. 6 is a flowchart of an example technique for identifying dislodgment of a ventricular lead during atrial fibrillation. The flowchart of FIGS. 6-10 are intended to illustrate the functional operation of IMD 10, medical system 8, and other devices and systems described herein, and should not be construed as reflective of a specific form of software or hardware necessary to practice the methods described. Methods described in conjunction with flow charts presented herein may be implemented in a non-transitory computer-readable medium that includes instructions for causing a programmable processor to carry out the methods described. A non-transitory computer-readable medium includes but is not limited to any volatile or non-volatile media, such as a RAM, ROM, CD-ROM, NVRAM, EEPROM, flash memory, or other computer-readable media, with the sole exception being a transitory, propagating signal. The instructions may be implemented as one or more software modules, which may be executed by themselves or in combination with other software.

The example methods illustrated by FIGS. 6-10 may be performed, by any one or more devices described herein, and may be performed, in part, by processing circuitry of any one or more devices described herein, such as by processing circuitry 106 of IMD 10, processing circuitry 140 of external device 30, processing circuitry 168 of server 164, or processing circuitry of access point 160 and/or computing devices 170. For ease of description, the methods of FIGS. 6-10 will be described hereafter as being performed by processing circuitry 106 of IMD 10.

According to the example method of FIG. 6, sensing circuitry 102 of IMD 10 senses a cardiac signal 190 via ventricular lead 20, e.g., a ventricular EGM signal (200). Processing circuitry 106 determines one or more characteristics of ventricular lead dislodgment during atrial fibrillation, such as an amplitude of R-waves 194 and/or variability of RR intervals (202). Processing circuitry 106 detects whether ventricular lead 20 is dislodged based on the one or more determined characteristics, e.g., based on the amplitude and/or variability satisfying respective thresholds (204). If processing circuitry 106 does not detect lead dislodgment (NO of 204), the processing circuitry continues to analyze the sensed cardiac signal (200, 202). If processing circuitry 106 detects lead dislodgment (YES of 204), processing circuitry 106 may provide an alert to a user, e.g., to external device 30 or another device via telemetry circuitry 118 (206).

Figure 7:
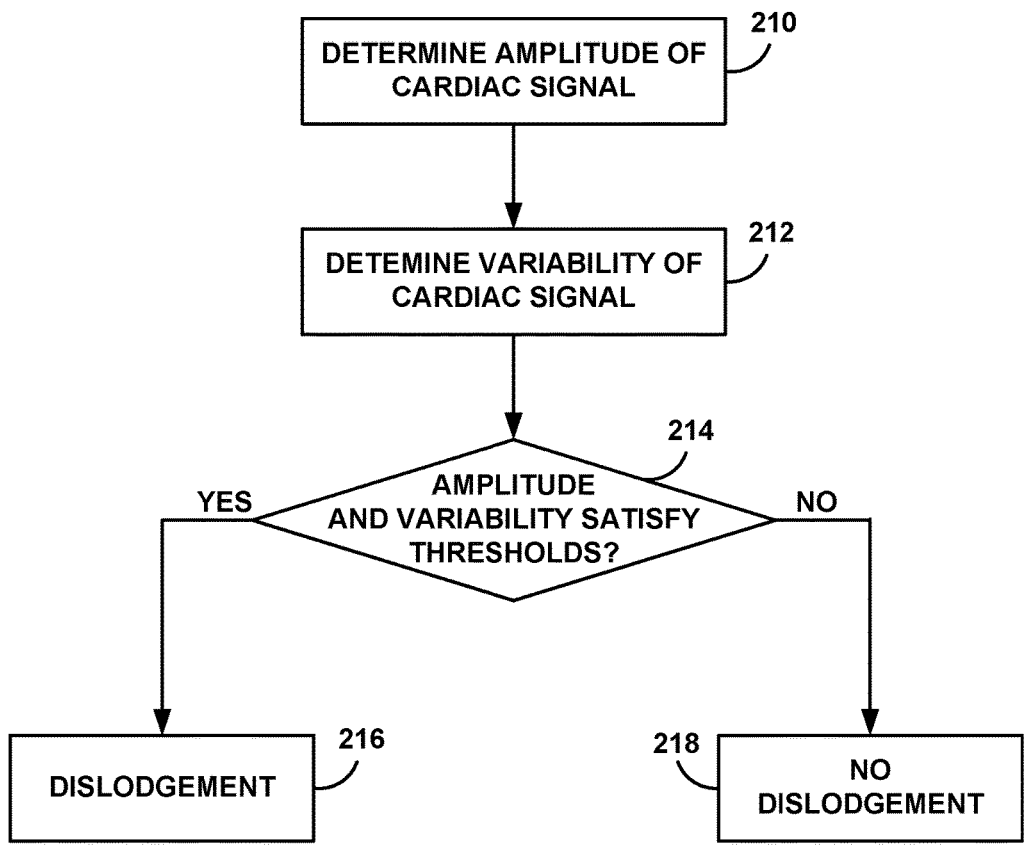
FIG. 7 is a flowchart of an example technique for determining characteristics of a cardiac signal sensed via a dislodged ventricular lead during atrial fibrillation.

FIG. 7 is a flowchart of an example technique for determining characteristics of a cardiac signal sensed via a dislodged ventricular lead during atrial fibrillation. The technique described in FIG. 7 may be used, for example, in blocks 202 and/or 204 of FIG. 6, FIG. 8 and/or FIG. 10. According to the example of FIG. 7, processing circuitry 106 determines an amplitude of cardiac signal 190, e.g., determines an amplitude of one or more of R-waves 194, as described with respect to FIG. 5 (210). Cardiac signal 190 may be a near-field ventricular EGM signal. Processing circuitry 106 also determines a variability of cardiac signal 190, e.g., determines one or more parameters indicating the variability of RR intervals 196, as described with respect to FIG. 5 (212).

Processing circuitry 106 determines whether the amplitude and variability satisfy respective thresholds (214). For example, processing circuitry 106 may determine whether an amplitude of a threshold percentage (e.g., 25%) of a group of R-waves 194 is less than an amplitude threshold (e.g., 1 mV). As another example, processing circuitry 106 may determine whether a modesum of consecutive RR intervals 196 is less than a modesum threshold (e.g., 50%) and/or a ratio of the maximum to the minimum of the consecutive RR intervals is greater than the ratio threshold (e.g., 2.0). Processing circuitry 106 detects dislodgement of ventricular lead 20 (216) based on the amplitude and variability meeting their respective thresholds (YES of 214), and does not detect dislodgement of ventricular lead 20 (218) based on the amplitude and/or variability not meeting their respective thresholds (NO of 214).

Figure 8:
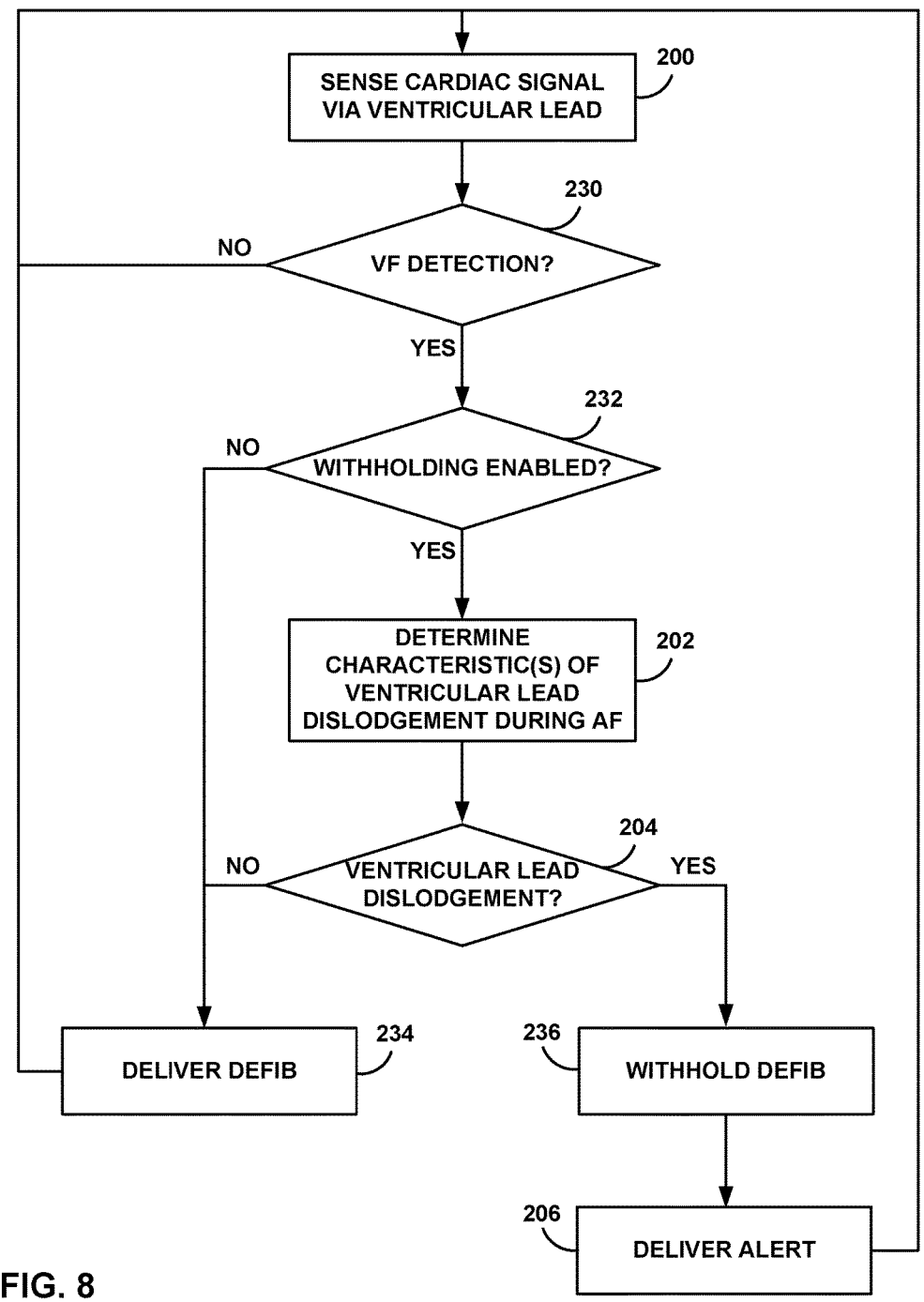
FIG. 8 is a flowchart of another example technique for identifying dislodgment of a ventricular lead during atrial fibrillation.

FIG. 8 is a flowchart of another example technique for identifying dislodgment of a ventricular lead during atrial fibrillation. The like-numbered blocks in FIG. 8 are described above in further detail with reference to FIG. 6.

According to the example of FIG. 8, sensing circuitry 102 of IMD 10 senses a cardiac signal 190 via ventricular lead 20, e.g., a ventricular EGM signal (200). Processing circuitry 106 determines whether ventricular fibrillation of heart 16 is detected based on cardiac signal 190 (230). Processing circuitry 106 may employ any technique for detecting ventricular fibrillation, e.g., based on the length of a number of RR intervals in an episode being less than a threshold length and/or other parameters, including signal morphology.

In response to detecting ventricular fibrillation, processing circuitry 106 determines whether a withholding feature is enabled (232). If the withholding feature is not enabled (NO of 232), processing circuitry 106 may control therapy delivery circuitry 104 to deliver a ventricular defibrillation therapy to treat the detected ventricular fibrillation (234). However, in some examples, processing circuitry 106 may perform other analyses not described in this disclosure to determine whether or not the defibrillation therapy should be withheld or delivered, whether or not the withholding feature described herein is enabled. Therefore, processing circuitry 106 does not necessarily control therapy delivery circuitry 104 to deliver the ventricular defibrillation therapy in response to the withholding feature not being enabled. Furthermore, in some examples, the withholding feature, and the determination as to whether the withholding feature is enabled (232), is optional, and may be excluded from the example technique of FIG. 8

If the withholding feature is enabled (YES of 232), or the withholding feature is omitted from the example technique and block 232 does not exist, processing circuitry 106 determines one or more characteristics of ventricular lead dislodgment during atrial fibrillation, such as an amplitude of R-waves 194 and/or variability of RR intervals (202). Processing circuitry 106 detects whether ventricular lead 20 is dislodged based on the one or more determined characteristics, e.g., based on the amplitude and/or variability satisfying respective thresholds (204). If processing circuitry 106 does not detect lead dislodgment (NO of 204), the processing circuitry may, but does not necessarily, control therapy delivery circuitry 104 to deliver the defibrillation therapy (234). If processing circuitry 106 detects lead dislodgment (YES of 204), the processing circuitry may control therapy delivery circuitry 104 to withhold the defibrillation therapy (236), and provide an alert to a user, e.g., to external device 30 or another device via telemetry circuitry 118 (206).

Figure 9:
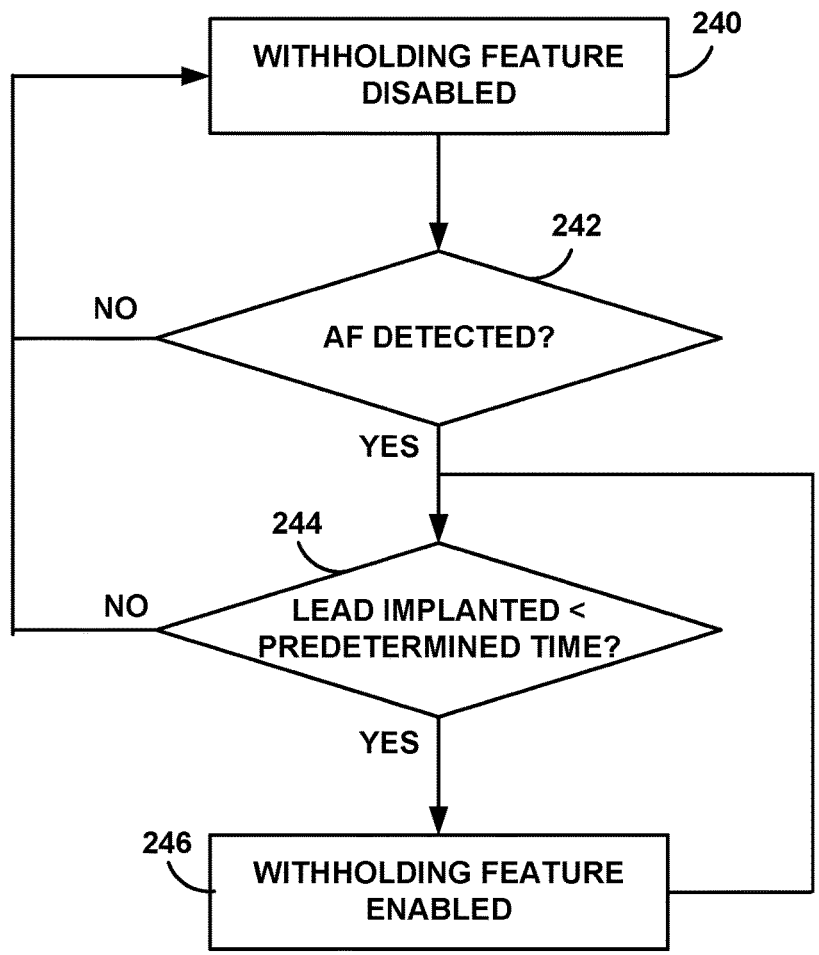
FIG. 9 is a flowchart of an example technique for determining whether a withholding feature is enabled or disabled.

FIG. 9 is a flowchart of an example technique for determining whether a withholding feature is enabled or disabled. The technique described in FIG. 9 may be used, for example, in block 232 of FIG. 8 and/or FIG. 10. According to the example technique of FIG. 9, processing circuitry 106 determines that the withholding feature is disabled (240) until an atrial fibrillation episode of heart 16 of patient 14 is detected (YES of 242) when ventricular lead 20 has been implanted for less than a predetermined time, e.g., 6 months (YES of 244). When these conditions are satisfied, processing circuitry 106 enables the withholding feature (246). However, when ventricular lead 20 has been implanted for at least the threshold period of time (NO of 244), processing circuitry 106 disables the withholding feature (240). In other examples, processing circuitry 106 may enable or disable the withholding feature based on only one of the conditions identified in FIG. 9, e.g., based either on whether lead 20 has been implanted less than a threshold period of time, or whether atrial fibrillation has previously been detected or has been detected within a threshold period of time in patient 14. In some examples, processing circuitry 106 may additionally or alternatively determine whether the withholding feature is enabled or not enabled in response to a user command, e.g., received from external device 30. Processing circuitry 106 may detect atrial fibrillation of heart 16 based on an atrial EGM from atrial lead 22, based on the ventricular EGM from ventricular lead 20, or may receive an indication of atrial fibrillation from another device, such as from a user via external device 30. Detection of atrial fibrillation of heart 16 based on the ventricular EGM from ventricular lead 20 may be, for example, according to algorithms that analyze characteristics of RR intervals 196 that reflect conduction of atrial fibrillation to the ventricles through the atrioventricular node, such as those employed by the Visia AF™ single chamber ICD available from Medtronic plc, of Dublin Ireland.

Figure 10:
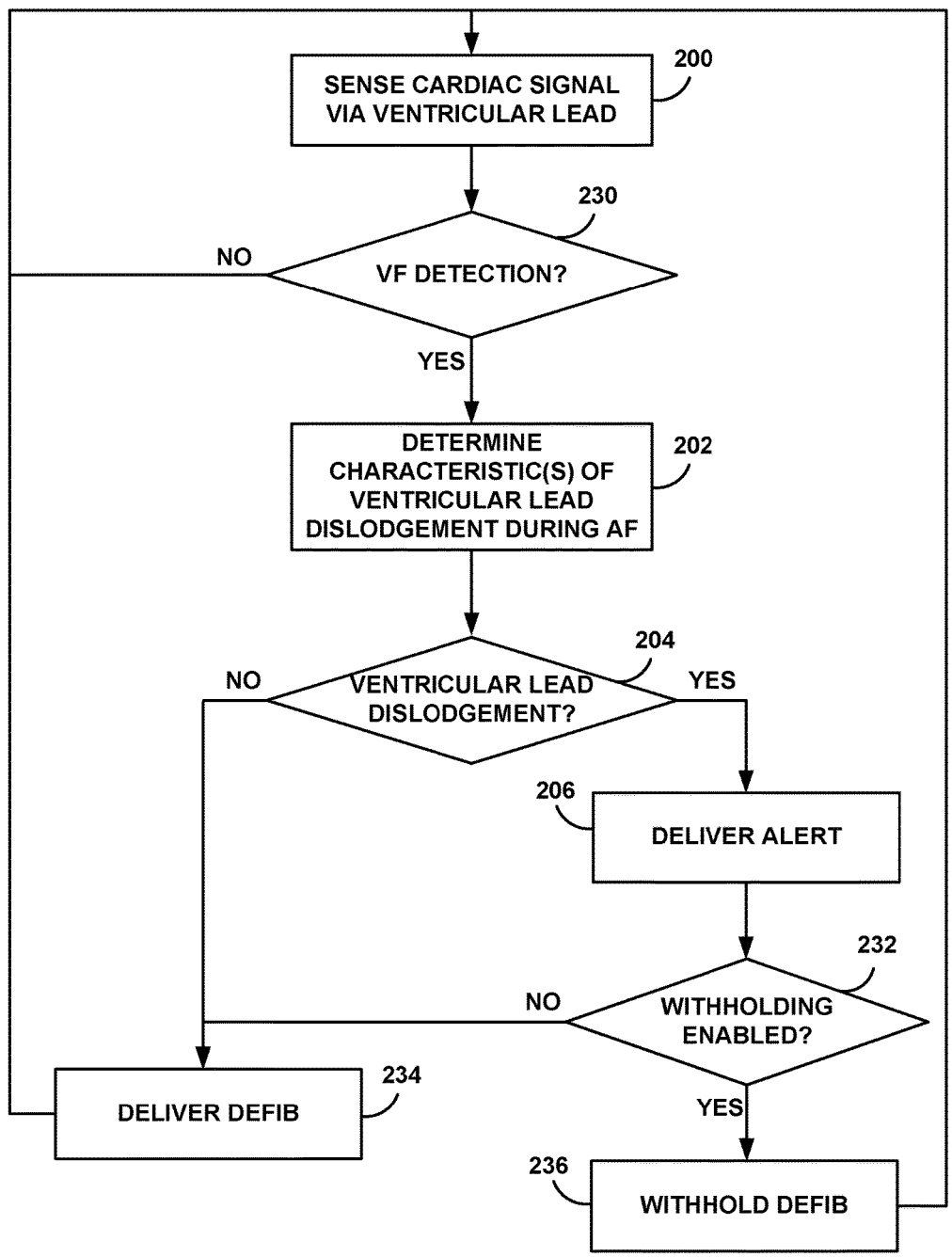
FIG. 10 is a flowchart of another example technique for identifying dislodgment of a ventricular lead during atrial fibrillation.

FIG. 10 is a flowchart of another example technique for identifying dislodgment of a ventricular lead during atrial fibrillation. The like-numbered blocks in FIG. 10 are described above in further detail with reference to FIG. 6 and/or FIG. 8.

According to the example technique of FIG. 10, sensing circuitry 102 of IMD 10 senses a cardiac signal 190 via ventricular lead 20, e.g., a ventricular EGM signal (200). Processing circuitry 106 determines whether ventricular fibrillation of heart 16 is detected based on cardiac signal 190 (230). In response to detecting ventricular fibrillation, processing circuitry 106 determines one or more characteristics of ventricular lead dislodgment during atrial fibrillation, such as an amplitude of R-waves 194 and/or variability of RR intervals (202). Processing circuitry 106 detects whether ventricular lead 20 is dislodged based on the one or more determined characteristics, e.g., based on the amplitude and/or variability satisfying respective thresholds (204).

If processing circuitry 106 does not detect lead dislodgment (NO of 204), the processing circuitry may, but does not necessarily, control therapy delivery circuitry 104 to deliver the defibrillation therapy (234). If processing circuitry 106 detects lead dislodgment (YES of 204), the processing circuitry may provide an alert to a user, e.g., to external device 30 or another device via telemetry circuitry 118 (206). Processing circuitry 106 also determines whether a withholding feature is enabled (232). If the withholding feature is not enabled (NO of 232), processing circuitry 106 may control therapy delivery circuitry 104 to deliver a ventricular defibrillation therapy to treat the detected ventricular fibrillation (234) despite having detecting detected dislodgement of ventricular lead 20, e.g., to avoid inappropriately withholding a needed therapy. If the withholding feature is enabled (YES of 232), processing circuitry may control therapy delivery circuitry 104 to withhold the defibrillation therapy (236).

In some examples, the withholding feature, and the determination as to whether the withholding feature is enabled (232), is optional, and may be excluded from the example technique of FIG. 10. In such examples, processing circuitry 106 may deliver the alert (206) and withhold the defibrillation therapy (236) in response to detecting ventricular lead dislodgment (YES of 204).

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various aspects of the disclosure have been described. These and other aspects are within the scope of the following claims.

What is claimed is:

1. A method of detecting dislodgement of a ventricular lead coupled to an implantable medical device, the method comprising:
   sensing, by sensing circuitry of the implantable medical device, a near-field cardiac signal via the ventricular lead;
   detecting, by processing circuitry, a ventricular fibrillation episode based on the sensed near-field cardiac signal;
   determining, by the processing circuitry, an amount of variability of detected RR intervals and an amplitude of the near-field cardiac signal in response to the ventricular fibrillation episode being detected;
   detecting, by the processing circuitry, dislodgement of the ventricular lead based on the amount of variability satisfying a variability threshold and the amplitude satisfying an amplitude threshold; and
   withholding, by the processing circuitry, delivery of a ventricular defibrillation therapy by the implantable medical device to treat the detected ventricular fibrillation based on detecting the dislodgement of the ventricular lead.

2. The method of claim 1, further comprising determining, by the processing circuitry, whether a lead dislodgement withholding feature is enabled, wherein
   withholding delivery of the ventricular defibrillation therapy to treat the detected ventricular fibrillation episode comprises withholding the delivery of the ventricular defibrillation therapy based on the withholding feature being enabled and detecting the dislodgement of the ventricular lead.

3. The method of claim 2, further comprising:
   determining, by the processing circuitry, that an atrial fibrillation episode has been detected; and
   enabling, by the processing circuitry, the withholding feature based on the atrial fibrillation episode being detected.

4. The method of claim 2, further comprising:
   determining, by the processing circuitry, whether the ventricular lead has been implanted for less than a predetermined time period; and
   enabling, by the processing circuitry, the withholding feature based on the ventricular lead being implanted for less than the predetermined time period.

5. The method of claim 2, further comprising controlling, by the processing circuitry, delivery of the ventricular defibrillation therapy by the implantable medical device based on detecting the dislodgement of the ventricular lead and the withholding feature being disabled.

6. The method of claim 1,
   wherein the amount of variability of detected RR intervals comprises at least one of:
      a modesum of the RR intervals, or
      a ratio of a maximum and a minimum of the RR intervals, and
   wherein detecting dislodgement of the ventricular lead based on the amount of variability satisfying a variability threshold comprises detecting dislodgement of the ventricular lead based on at least one of:
      the modesum being less than a predetermined modesum percentage, or
      the ratio being at least a ratio threshold.

7. The method of claim 1, wherein determining an amplitude of the near-field cardiac signal comprises determining an amplitude for each of a plurality of detected R-waves, and wherein detecting dislodgement of the ventricular lead based on the amplitude satisfying an amplitude threshold comprises detecting dislodgement of the ventricular lead based on the amplitude of a threshold number of detected R-waves being less than the amplitude threshold.

8. The method of claim 1, wherein determining at least one characteristic of the near-field cardiac signal associated with dislodgement of the ventricular lead during an atrial fibrillation episode further comprises determining an amplitude of the near-field cardiac signal, and wherein detecting dislodgement of the ventricular lead comprises detecting dislodgement of the ventricular lead based on the amplitude being less than an amplitude threshold.

9. The method of claim 8, wherein determining an amplitude of the near-field cardiac signal comprises determining an amplitude for each of a plurality of detected R-waves, and wherein detecting dislodgement of the ventricular lead based on the amplitude satisfying an amplitude threshold comprises detecting dislodgement of the ventricular lead based on the amplitude of a threshold number of detected R-waves being less than the amplitude threshold.

10. The method of claim 1, wherein increased amount of variability of detected RR intervals comprises increased irregularity of timing between consecutively detected R-waves.

11. The method of claim 1,
    wherein the amount of variability of detected RR intervals comprises:
       a modesum of the RR intervals, and
       a ratio of a maximum and a minimum of the RR intervals, and
    wherein detecting dislodgement of the ventricular lead based on the increased amount of variability of detected RR intervals above a threshold amount of variability comprises detecting dislodgement of the ventricular lead based on:
       the modesum being less than a predetermined modesum percentage, and
       the ratio being at least a ratio threshold.

12. A medical device system comprising:
    a ventricular lead comprising a plurality of electrodes; and
    sensing circuitry configured to sense a cardiac signal via at least one of the plurality of electrodes of the ventricular lead;
    therapy delivery circuitry configured to deliver a ventricular defibrillation therapy; and
    processing circuitry configured to:
       detect a ventricular fibrillation episode based on the sensed cardiac signal;
       determine at least one characteristic of the cardiac signal associated with dislodgement of the ventricular lead during atrial fibrillation in response to the ventricular fibrillation episode being detected, wherein the at least one characteristic comprises an increased amount of variability of detected RR intervals above a threshold amount of variability;
       detect dislodgement of the ventricular lead based on the determined at least one characteristic;
       provide a lead dislodgement alert in response to detecting the dislodgement of the ventricular lead; and withhold delivery of the ventricular defibrillation therapy by the therapy delivery circuitry to treat the detected ventricular fibrillation based on detecting the dislodgement of the ventricular lead,
wherein the processing circuitry is further configured to:
determine whether the ventricular lead has been implanted for less than a predetermined time period;
enable a lead dislodgement withholding feature based on the ventricular lead being implanted for less than the predetermined time period; and
at least one of:
determine the at least one characteristic of the cardiac signal associated with dislodgement of the ventricular lead during atrial fibrillation in response to the withholding feature being enabled and the ventricular fibrillation episode being detected; or
withhold the delivery of the ventricular defibrillation therapy by the therapy delivery circuitry to treat the detected ventricular fibrillation episode based on the withholding feature being enabled and detecting the dislodgement of the ventricular lead.

13. The system of claim 12, wherein the processing circuitry is configured to determine whether an atrial fibrillation episode has been detected, and enable the withholding feature based on the atrial fibrillation episode being detected.

14. The system of claim 12, wherein the processing circuitry is configured to control the therapy delivery circuitry to deliver the ventricular defibrillation therapy based on the ventricular episode being detected and the withhold feature being disabled.

15. The system of claim 12,
wherein the amount of variability of detected RR intervals comprises at least one of:
a modesum of the RR intervals or a ratio of a maximum, and
a minimum of the RR intervals, or
wherein the processing circuitry is configured to detect dislodgement of the ventricular lead based on at least one of:
the modesum being less than a predetermined modesum percentage, or
the ratio being at least a ratio threshold.

16. The system of claim 15, wherein the cardiac signal comprises a near-field cardiac signal, wherein the at least one characteristic of the near-field cardiac signal associated with dislodgement of the ventricular lead during atrial fibrillation further comprises an amplitude of the cardiac signal, and wherein the processing circuitry is configured to detect dislodgement of the ventricular lead based on the amplitude being less than an amplitude threshold.

17. The system of claim 16, wherein the processing circuitry is configured to:
determine an amplitude for each of a plurality of detected R-waves; and
detect dislodgement of the ventricular lead based on the amplitude of a threshold number of the detected R-waves being less than the amplitude threshold.

18. The system of claim 12, wherein the cardiac signal comprises a near-field cardiac signal, wherein the at least one characteristic of the near-field cardiac signal associated with dislodgement of the ventricular lead during atrial fibrillation comprises an amplitude of the cardiac signal, and wherein the processing circuitry is configured to detect dislodgement of the ventricular lead based on the amplitude being less than an amplitude threshold.

19. The system of claim 18, wherein the processing circuitry is configured to:
determine an amplitude for each of a plurality of detected R-waves; and
detect dislodgement of the ventricular lead based on the amplitude of a threshold number of the detected R-waves being less than the amplitude threshold.

20. The medical device system of claim 12, wherein amount of increased variability of detected RR intervals comprises increased irregularity of timing between consecutively detected R-waves.

21. The system of claim 12,
wherein the amount of variability of detected RR intervals comprises:
a modesum of the RR intervals or a ratio of a maximum, and
a ratio of a maximum and a minimum of the RR intervals, and
wherein the processing circuitry is configured to detect dislodgement of the ventricular lead based on:
the modesum being less than a predetermined modesum percentage, and
the ratio being at least a ratio threshold.

22. A non-transitory computer-readable medium comprising instructions that, when executed by processing circuitry, cause the processing circuitry to:
determine at least one characteristic of a near-field cardiac signal sensed via a ventricular lead;
detect a ventricular fibrillation episode based on the sensed near-field cardiac signal;
determine an amount of variability of detected RR intervals of the near-field cardiac signal and an amplitude of the near-field cardiac signal in response to the ventricular fibrillation episode being detected;
detect dislodgement of the ventricular lead based on the amount of variability satisfying a threshold amount of variability and the amplitude satisfying an amplitude threshold;
and
withhold delivery of a ventricular defibrillation therapy by therapy delivery circuitry to treat the detected ventricular fibrillation episode based on the detection of dislodgement of the ventricular lead.

23. A medical device system comprising:
a ventricular lead comprising a plurality of electrodes; and
an implantable medical device coupled to the ventricular lead, the implantable medical device comprising:
sensing circuitry configured to sense a near-field cardiac signal via at least one of the plurality of electrodes;
therapy delivery circuitry configured to deliver a ventricular defibrillation therapy;
processing circuitry configured to:
detect a ventricular fibrillation episode based on the sensed near-field cardiac signal;
determine an amount of variability of RR intervals of the near-field cardiac signal and an amplitude of the near-field cardiac signal in response to the ventricular fibrillation episode being detected;
detect dislodgement of the ventricular lead based on the amount of variability satisfying a variability threshold and the amplitude satisfying an amplitude threshold; and withhold delivery of a ventricular defibrillation therapy by the therapy delivery circuitry to treat the detected ventricular fibrillation episode based on the detection of dislodgement of the ventricular lead.

24. The system of claim 23, wherein the processing circuitry is configured to:
   determine a modesum of the RR intervals; and
   detect dislodgement of the ventricular lead based on the modesum being less than a predetermined modesum percentage.

25. The system of claim 23, wherein the processing circuitry is configured to:
   determine a ratio of a maximum and a minimum of the RR intervals; and
   detect dislodgement of the ventricular lead based on the ratio satisfying a ratio threshold.

26. The system of claim 23, wherein the processing circuitry is configured to:
   determine an amplitude for each of a plurality of detected R-waves; and
   detect dislodgement of the ventricular lead based on the amplitude of a threshold number of the detected R-waves being less than the amplitude threshold.

27. The medical device system of claim 23, wherein an amount of variability of detected RR intervals comprises increased irregularity of timing between consecutively detected R-waves.

* * * * *